US011365170B2

(12) United States Patent
Yamaguchi et al.

(10) Patent No.: US 11,365,170 B2
(45) Date of Patent: Jun. 21, 2022

(54) NON-SOLVATE CRYSTAL OF EUCOMIC ACID AND METHOD FOR PRODUCING SAME

(71) Applicant: KYOWA HAKKO BIO CO., LTD., Tokyo (JP)

(72) Inventors: Yuta Yamaguchi, Tokyo (JP); Hiroshi Nagano, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 17/259,877

(22) PCT Filed: Jul. 12, 2019

(86) PCT No.: PCT/JP2019/027790
§ 371 (c)(1),
(2) Date: Jan. 12, 2021

(87) PCT Pub. No.: WO2020/013330
PCT Pub. Date: Jan. 16, 2020

(65) Prior Publication Data
US 2021/0221764 A1    Jul. 22, 2021

(30) Foreign Application Priority Data
Jul. 13, 2018    (JP) .............................. JP2018-133057

(51) Int. Cl.
*C07C 51/43*    (2006.01)
*C07C 59/52*    (2006.01)

(52) U.S. Cl.
CPC .......... *C07C 51/43* (2013.01); *C07B 2200/13* (2013.01); *C07C 59/52* (2013.01)

(58) Field of Classification Search
CPC ..... C07C 59/52; C07C 51/43; C07B 2200/13; C07B 2200/07
See application file for complete search history.

(56) References Cited

U.S. PATENT DOCUMENTS

| 5,442,051 | A | 8/1995 | Ozeki et al. | |
| 6,605,729 | B1 * | 8/2003 | Byrn | A61P 3/06 548/537 |
| 8,158,780 | B2 * | 4/2012 | Phull | C07J 71/0031 540/63 |
| 2007/0225314 | A1 | 9/2007 | Diulgheroff et al. | |
| 2011/0046183 | A1 * | 2/2011 | Hashimoto | A61P 31/04 546/273.4 |
| 2012/0108625 | A1 | 5/2012 | Diulgheroff et al. | |
| 2012/0165364 | A1 * | 6/2012 | Diulgheroff | A61P 25/00 514/291 |
| 2013/0157968 | A1 | 6/2013 | Simmler et al. | |
| 2014/0057935 | A1 | 2/2014 | Diulgheroff et al. | |

FOREIGN PATENT DOCUMENTS

| JP | H03-157393 | A | 7/1991 |
| JP | 2009-513675 | A | 4/2009 |
| JP | 2011-513202 | A | 4/2011 |
| JP | 2014-045756 | A | 3/2014 |
| WO | WO 2011/125057 | A1 | 10/2011 |

OTHER PUBLICATIONS

Li et al. (Eucomic acid methanol monosolvate, Acta Crystallographica Section E, Structure Reports, Organic Compounds, with supporting information, totals pp. 6, Published 2011) (Year: 2011).*
Simmler et al. (Glucosyloxybenzyl Eucomate Derivatives from *Vanda teres* Stimulate HaCaT Cyochrome c Oxidase, Journal of Natural Products, 74, pp. 949-955, Published 2011) (Year: 2011).*
Heller et al., "Isolierung, Konstitution und Synthese der (R)-(−)-Eucominsäure," *Helv. Chim. Acta.*, 57(6): 1766-1784 [No. 189] (1974).
Li et al., "Eucomic acid methanol monosolvate," *Acta. Crystallogr. Sect. E. Struct. Rep. Online*, E67(8): o2192 (2011).
Okada et al., "(R)-Eucomic acid, a leaf-opening factor of the model organism, *Lotus japonicus*," *Tetrahedron*, 65: 2136-2141 (2009).
Simmler et al., "Glucosyloxybenzyl Eucomate Derivatives from *Vanda teres* Stimulate HaCaT Cytochrome c Oxidase," *J. Nat. Prod.*, 74(5): 949-955 (2011).
Japanese Patent Office, International Search Report in International Patent Application No. PCT/JP2019/027790 (dated Oct. 15, 2019).
Japanese Patent Office, Written Opinion of the International Searching Authority in International Patent Application No. PCT/JP2019/027790 (dated Oct. 15, 2019).
Japanese Patent Office, Notice of Reasons for Refusal in Japanese Patent Application No. 2020-530285 (dated Dec. 14, 2021).
Kegg Drug Database, Ciclesonide Catalog Entry (Nov. 17, 2021) [obtained online at: https://www-kegg-jp.translate.goog/medicus-bin/japic_med?japic_code=00059259&_x_tr_sl=ja&_x_tr_tl=en&_x_tr_hl=ja].
Harris et al., "Isolation of 2-(4-Hydroxybenzyl)malic acid from *Petalostemon gattingeri*," *J. Org. Chem.*, 38(26): 4457-4459 (1973).
Koizumi et al., "Isolation of 2-(4-Hydroxybenzyl)malic acid from *Lycoris radiata*," *Phytochemistry*, 15: 342-343 (1976).
European Patent Office, Extended European Search Report in European Patent Application No. 19835137.1 (dated Mar. 16, 2022).
Head of Ministry of Health and Welfare, "Guidelines for Residual Solvents in Pharmaceutical Products," Pharmaceutical Trial No. 307 (1998)14 pages.
Ogata, "Chemical Experimental Procedures," vol. 1, pp. 366-399 (27th edition, published by Nankodo Co., Ltd., 1963) 47 total pages.
Japanese Patent Office, Decision of Refusal in Japanese Patent Application No. 2020-530285 (dated Apr. 12, 2022) 7 pages.

* cited by examiner

*Primary Examiner* — Yevgeny Valenrod
*Assistant Examiner* — Blaine G Doletski
(74) *Attorney, Agent, or Firm* — Leydig, Voit & Mayer, Ltd.

(57) ABSTRACT

An object of the present invention is to provide a non-solvate crystal of eucomic acid having a low methanol content and excellent fluidity, and a method for producing the same. The present invention can provide a non-solvate crystal of eucomic acid having a low methanol content and excellent fluidity by drying a methanol solvate crystal of eucomic acid.

7 Claims, 2 Drawing Sheets

NON-SOLVATE CRYSTAL OF EUCOMIC ACID AND METHOD FOR PRODUCING SAME

CROSS-REFERENCE TO RELATED APPLICATIONS

This patent application is the U.S. national phase of International Patent Application No. PCT/JP2019/027790, filed Jul. 12, 2019, which claims the benefit of Japanese Patent Application No. 2018-133057, filed on Jul. 13, 2018, which are incorporated by reference in their entireties herein.

TECHNICAL FIELD

The present invention relates to a non-solvate crystal of eucomic acid and a method for producing the same.

BACKGROUND ART

Eucomic acid ((R)-2-hydroxy-2-[(4-hydroxyphenyl)methyl]butanedioic acid) is a compound contained in a plant such as bird's-foot trefoil, and is a compound discovered from a bulb extract of *Eucomis punctata* (Non-Patent Document 1).

Eucomic acid or a derivative thereof is recognized to have an antiaging effect on skin (Non-Patent Document 2 and Patent Document 1), and hence eucomic acid is useful as, for example, a raw material or an intermediate of cosmetics.

Up till now, a method by chemical synthesis (Non-Patent Document 3) and a method by extraction from a plant have been reported (Non-Patent Document 4) as a method for producing eucomic acid. In Patent Document 2, eucomic acid is disclosed as an intermediate when L-homo tyrosine is produced by using microorganisms. On the other hand, in Non-Patent Document 4, a mono-methanol solvate crystal is disclosed as a crystal of eucomic acid, but powder properties of the crystal are not disclosed at all.

RELATED ART

Patent Document

Patent Document 1: WO2011/125057
Patent Document 2: JP-A-2014-45756

Non-Patent Document

Non-Patent Document 1: Helv. Chim. Acta, 1974, 57, 1766-1784
Non-Patent Document 2: J. Nat. Prod., 2011, 74(5), 949-955
Non-Patent Document 3: Tetrahedron. 2009, 65, 2136-2141
Non-Patent Document 4: Acta Cryst., 2011, E67, o2192

DISCLOSURE OF INVENTION

Problems to be Solved by the Invention

As the crystal of eucomic acid, there are only reports on the mono-methanol solvate crystal till now. However, since methanol is harmful to a human body, it is desired that methanol does not remain in the crystal as far as possible. In addition, although the powder properties of the mono-methanol solvate crystal are not known, a crystal of eucomic acid having excellent fluidity is desired from the viewpoint of industrial handling.

Therefore, an object of the present invention is to provide a non-solvate crystal of eucomic acid having a low methanol content and excellent fluidity, and a method for producing the same.

Means for Solving the Problems

The present invention relate to the following (1) to (9).
(1) A non-solvate crystal of eucomic acid.
(2) The crystal according to (1), which has peaks at diffraction angle 2θ (°) of $13.1°±0.2°$, $18.7°±0.2°$, and $21.8°±0.2°$ in powder X-ray diffraction.
(3) The crystal according to (2), which further has peaks at diffraction angle 2θ (°) of $22.6°±0.2°$, $33 8°±0.2°$, and $10.9±0.2°$ in powder X-ray diffraction.
(4) The crystal according to (3), which further has peaks at diffraction angle 2θ (°) of $26.7°±0.2°$, $27.6°±0.2°$, and $18.2°±0.2°$ in powder X-ray diffraction.
(5) The crystal according to (4), which further has peaks at diffraction angle 2θ (°) of $33.3°±0.2°$, $37.3°±0.2°$, $26.3°±0.2°$, and $34.8°±0.2°$ in powder X-ray diffraction.
(6) The crystal according to (5), which further has peaks at diffraction angle 2θ (°) of $31.1°±0.2°$, $36.9°±0.2°$, and $38.6°±0.2°$ in powder X-ray diffraction.
(7) The crystal according to (6), which further has peaks at diffraction angle 2θ (°) of $16.1°±0.2°$, $23.5°±0.2°$, and $31.4°±0.2°$ in powder X-ray diffraction.
(8) A method for producing a non-solvate crystal of eucomic acid, comprising a step of drying a methanol solvate crystal of eucomic acid.
(9) A method for producing a non-solvate crystal of eucomic acid, comprising: a step of dropping or adding methanol or an aqueous methanol solution to an aqueous solution in which eucomic acid is dissolved to precipitate a methanol solvate crystal of eucomic acid in the aqueous solution: a step of collecting the methanol solvate crystal of eucomic acid from the aqueous solution, and a step of drying the collected methanol solvate crystal of eucomic acid.

EMBODIMENTS FOR CARRYING OUT THE INVENTION

1. Crystal of Present Invention

Figure 1:
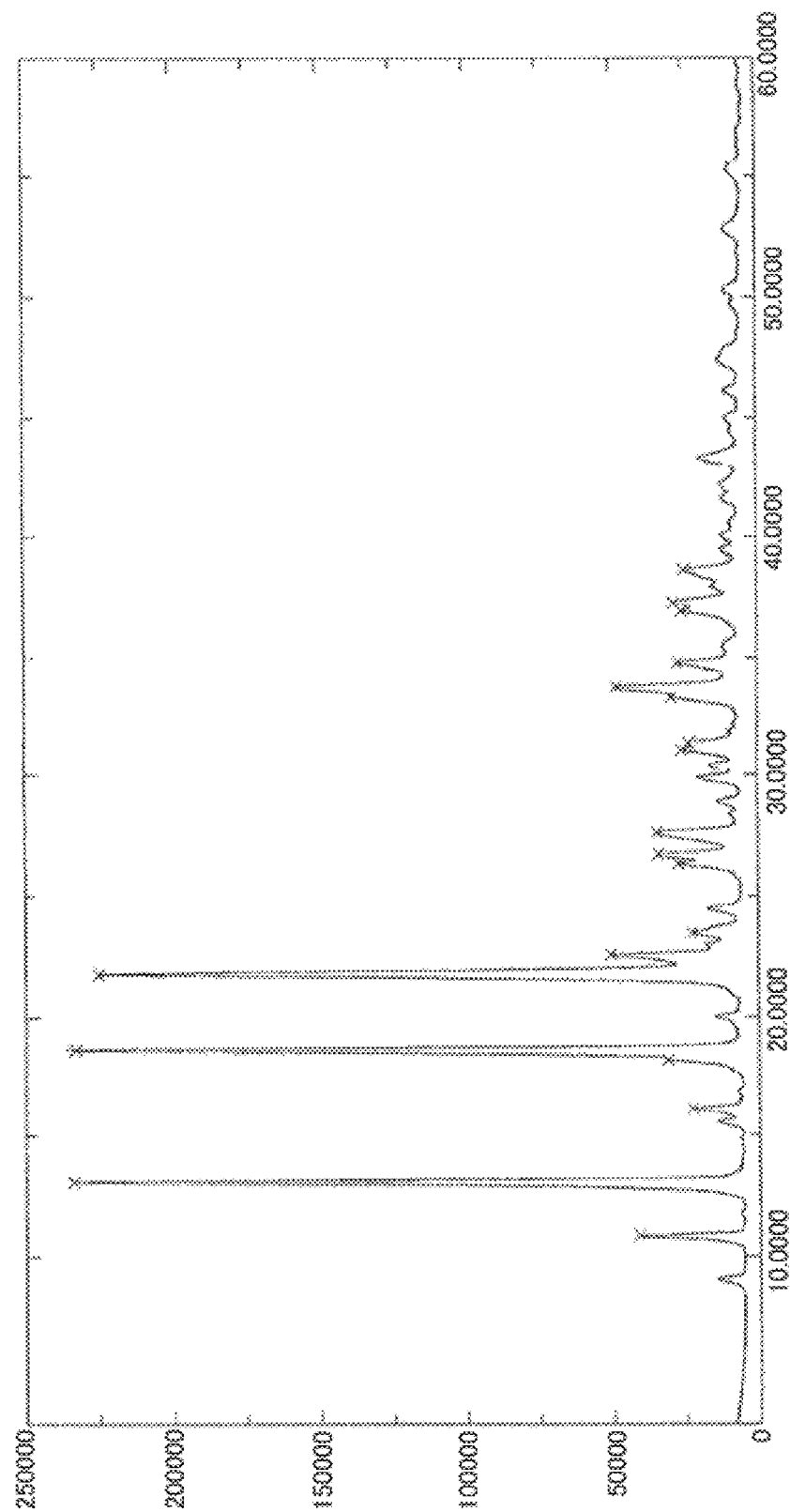
FIG. 1 shows results of powder X-ray diffraction of a non-solvate crystal of eucomic acid obtained in Examples. A vertical axis represents an intensity (cps), and a horizontal axis represents a diffraction angle 2θ (°).

The crystal of the present invention is a non-solvate crystal of eucomic acid. The non-solvate crystal refers to a crystal that does not contain or hardly contains an organic solvent such as alcohol, acetone, or hexane and a solvent such as water in the crystal.

The fact that the crystal hardly contains an organic solvent means that a content of the organic solvent in the crystal is preferably 0.25 wt % or less, more preferably 0.20 wt % or less, and most preferably 0.15 wt % or less.

The fact that the crystal hardly contains water means that a content of water in the crystal is preferably 2.0 wt % or less, more preferably 1.0 wt % or less, and most preferably 0.5 wt % or less.

Examples of a method for confirming that a crystal is the crystal of the present invention include the following methods (a) to (d).
(a) The fact that the crystal does not contain or hardly contains an organic solvent can be confirmed by analyzing the crystal by a method using a gas chromatograph as described below, for example, to measure a methanol content.

Analysis Example Using Gas Chromatograph

Used equipment: GC-2014 (manufactured by Shimadzu Corporation)
Column: AGILENT J&W DB-WAX 30 m×0.535 mm×1.00 μm (Agilent Technologies, Inc.)
Column temperature: 200° C.
Carrier gas: helium
Flow rate: 33.0 mL/min
(b) The fact that the crystal does not contain or hardly contains water can be confirmed by measuring a water content in the crystal by Karl Fischer method as described below.

Measurement Example by Karl Fischer Method

Used equipment: AQV-2200 (HIRANUMA SANGYO Co., Ltd.)
Measurement method: The water content in the crystal is measured in accordance with instructions for use of AQV-2200 (HIRANUMA SANGYO Co., Ltd.)
(c) The fact that the crystal is a crystal of eucomic acid can be confirmed by analysis using, for example, high performance liquid chromatography (HPLC). Such analysis examples using HPLC include the following conditions.

Analysis Example Using HPLC

Column: Develosil ODS-HG5 4.6×250 mm (manufactured by Nomura Chemical Co, Ltd.), column temperature: 40° C.
Flow rate: 1.0 mL/min
Mobile phase: a solution in which water, methanol, and 26 mol/L of formic acid aqueous solution are mixed in volume ratio of 80:20:0.1
Detector: UV detector (detection wavelength. 220 nm)
(d) The fact that the crystal is a crystal of eucomic acid can also be confirmed by analysis by powder X-ray diffraction.
The analysis by powder X-ray diffraction can be performed in accordance with the accompanying instructions for use by using, for example, a powder X-ray diffraction device (XRD) Ultima IV (manufactured by Rigaku Corporation) and using CuKα as an X-ray source.
Examples of the crystal of the present invention include a crystal having peaks at diffraction angle 2θ (°) described in the following (1) in the powder X-ray diffraction using CuKα as an X-ray source, preferably a crystal having peaks at diffraction angle 2θ (°) described in the following (1) and (II), more preferably a crystal having peaks at diffraction angle 2θ (°) described in the following (I) to (III), further more preferably a crystal having peaks at diffraction angle 2θ (°) described in the following (I) to (IV), particularly preferably a crystal having peaks at diffraction angle 2θ (°) described in the following (I) to (V), and most preferably a crystal having peaks at diffraction angle 2θ (°) described in the following (I) to (VI).

(I) 13.1°±0.2°, preferably ±0.1°, 18.7°±0.2°, preferably ±0.1°, and 21.8°±0.2°, preferably ±0.1°
(II) 22.6°±0.2°, preferably ±0.1°, 33.8°±0.2°, preferably ±0.1°, and 10.9°±0.2°, preferably ±0.1°
(III) 26.7°±0.2°, preferably ±0.1°, 27 6°±0.2°, preferably ±0.1°, and 18.2°±0.2°, preferably ±0.1°
(IV) 33.3°±0.2°, preferably ±0.1°, 37.3±0.2°, preferably ±0.1°, 26.3°±0.2°, preferably ±0°, and 34.8°±0.2°, preferably ±0.1°
(V) 31.1°±0.2°, preferably ±0.1°, 36.9°±0.2°, preferably ±0.1°, and 38.6°±0.2°, preferably ±0.1°
(VI) 16.1°±0.2°, preferably ±0.1°, 23.5°±0.2°, preferably ±0.1°, and 31.4°±0.2°, preferably ±0.1°

One embodiment of the crystal of the present invention include a non-solvate crystal of eucomic acid which has peaks at the above diffraction angle 2θ (°) in powder X-ray diffraction using CuKα as an X-ray source, and has an angle of repose of preferably 45 degrees or less, more preferably 44 degrees or less, still more preferably 42 degrees or less, and most preferably 40 degrees or less.

The angle of repose refers to an angle formed by a generating line of a cone formed with a powder when the powder is allowed to gently fall onto the horizontal plane through a kind of funnel and a horizontal plane.

Since the crystal having a large angle of repose has poor fluidity, for example, the crystal cannot be completely discharged from a hopper bottom unless an inclination angle of the hopper bottom is larger than the angle of the repose when the crystal is discharged from the hopper in a filling step of the crystal to a packaging container, the type of the hopper that can be used is limited, and a device that assists the discharge of the crystal is required. Therefore, the angle of repose of the crystal is preferably small.

The angle of repose can be measured using Multi Tester MT-1001T (manufactured by Seishin Enterprise Co, Ltd.) in accordance with the accompanying manual according to the following measurement example.

Measurement Example of Angle of Repose

Used equipment: multi-tester MT-1001T type (manufactured by Seishin Enterprise Co., Ud.)
Sieve: 1.18 mm
Vibration width: 0.5 to 0.6 mm
Measurement method: Crystals are allowed to fall by passing through a sieve of 1.18 mm that is vibrated with a width of 0.5 to 0.6 mm, and are deposited on an angle-of-repose table (part number: MT-1029). The angle-of-repose table is rotated without being given vibration, angles are read at three sites, and an arithmetic mean value of the angles is determined to be the angle of repose.

One embodiment of the crystal of the present invention include a non-solvate crystal of eucomic acid which has peaks at the above diffraction angle 2θ (°) in powder X-ray diffraction using CuKα as an X-ray source and, has a uniformity coefficient of preferably 4.00 or less, more preferably 3.80 or less, still more preferably 3.60 or less, and most preferably 3.40 or less.

The uniformity coefficient is an index representing fluidity of the powder, and refers to a ratio obtained by dividing a particle diameter through which the powder in an amount of 60% passes by a particle diameter through which the powder in an amount of 10% passes on a cumulative particle diameter distribution curve measured by particle size distribution measurement or sieve division. The closer the value of the uniformity coefficient is to 1, the higher the fluidity is.

The uniformity coefficient can be measured in accordance with the accompanying manual using, for example, a particle size distribution measuring device LS 13 32 (manufactured by Beckman Coulter, Inc.).

One embodiment of the crystal of the present invention include the non-solvate crystal of eucomic acid in which the powder X-ray diffraction pattern using CuKα as the X-ray source and is defined by the pattern shown in FIG. 1 and the values of the diffraction angle shown in Table 1.

Figure 2:
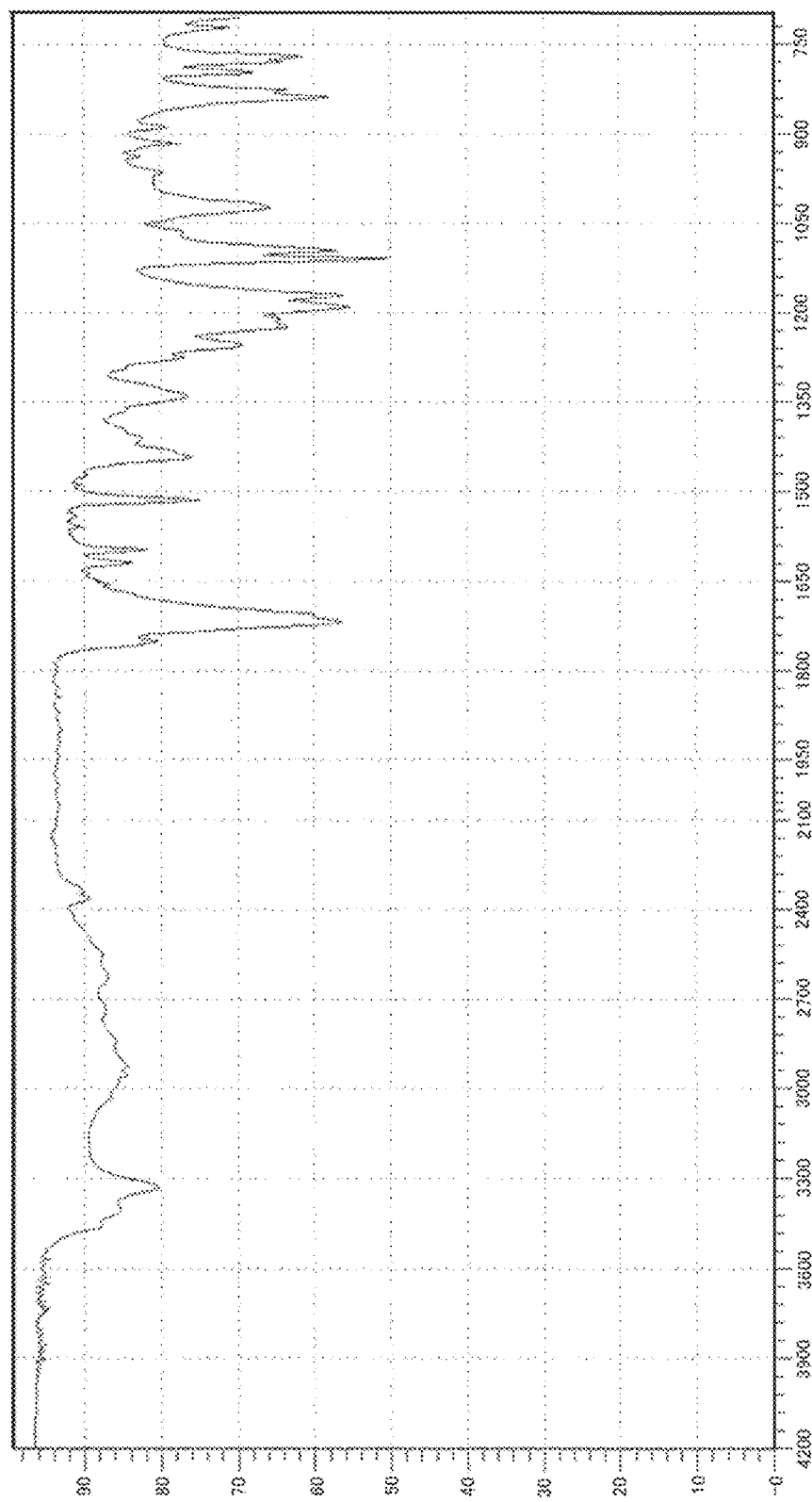
FIG. 2 shows results of infrared (IR) spectroscopic analysis of the non-solvate crystal of eucomic acid obtained in Examples. A vertical axis represents light transmittance (% T), and a horizontal axis represents a wave number (1/cm).

In addition, when provided for infrared (IR) spectroscopic analysis, one embodiment of the crystal of the present invention also include the non-solvate crystal of eucomic acid showing an infrared absorption spectrum shown in FIG. 2.

Infrared (IR) spectroscopic analysis can be performed in accordance with the accompanying instructions for use by using, for example, an FTIR-8400 type (manufactured by Shimadzu Corporation).

2. Production Method-1 of Present Invention

The production method of the present invention is a method for producing a non-solvate crystal of eucomic acid, comprising a step of drying a methanol solvate crystal of eucomic acid.

Examples of the methanol solvate crystal of eucomic acid include a mono-methanol solvate crystal of eucomic acid. The mono-methanol solvate crystal of eucomic acid can be obtained in accordance with, for example, a method described in [Acta Cryst., 2011, E67, o2192] or a method described in the following 3.

The fact that the methanol solvate crystal of eucomic acid is a mono-methanol solvate crystal can be confirmed by the fact that a methanol content in the crystal except for methanol adhering to a crystal surface thereof is generally 7.0 to 14.0 wt %, preferably 9.0 to 11.0 wt %.

The methanol content in the crystal except for the methanol adhering to the crystal surface can be measured by, for example, thermal analysis described in the following measurement example.

Measurement Example of Methanol Content in Crystal by Thermal Analysis

Used equipment: EXSTAR 6000 TG/DTA 6200 (manufactured by Seiko Instruments Inc.)

Measurement conditions: Temperature rises from 20° C. to 30° C. at 20° C./min→Hold for 15 minutes at 30° C.→Temperature rises from 30° C. to 250° C. at 5° C./min Nitrogen flow rate: 300 mL/min Sampling interval: 0.5 s Examples of a drying method in a step of drying the methanol solvate crystal of eucomic acid include heating and drying Examples of a drying temperature when the methanol solvate crystal of eucomic acid is heated and dried include generally 80° C. to 150° C., preferably 85° C. to 130° C., more preferably 90'C to 110° C.

Time required for heating and drying varies with the drying temperature, but can be appropriately set by a person skilled in the art within a range of, for example, generally 2 to 100 hours, preferably 3 to 70 hours, and most preferably 5 to 50 hours, as long as it is time for the methanol to be desorbed without decomposing the methanol solvate crystal of eucomic acid.

Examples of purity of the non-solvate crystal of eucomic acid which can be produced by the "production method-1 of the present invention" include generally 95% or more, preferably 96% or more, more preferably 97% or more, and most preferably 98% or more.

The purity of the non-solvate crystal of eucomic acid can be confirmed by, for example, analysis using HPLC of the above 1.

Examples of the non-solvate crystal of eucomic acid which can be produced by the "production method-1 of the present invention" include the non-solvate crystal of eucomic acid which has the powder X-ray diffraction pattern using CuKα as the X-ray source and is defined by the pattern shown in FIG. 1 and the values of the diffraction angle shown in Table 1.

Examples of the non-solvate crystal of eucomic acid which can be produced by the "production method-1 of the present invention" can also include the non-solvate crystal of eucomic acid showing an infrared absorption spectrum shown in FIG. 2 when provided for infrared (R) spectroscopic analysis.

3. Production Method-2 of Present Invention

Examples of the production method of the present invention can also include a method for producing the non-solvate crystal of eucomic acid, comprising a step of dropping or adding methanol or an aqueous methanol solution to an aqueous solution in which eucomic acid is dissolved to precipitate a methanol solvate crystal of eucomic acid in the aqueous solution, a step of collecting the methanol solvate crystal of eucomic acid from the aqueous solution, and a step of drying the collected methanol solvate crystal of eucomic acid.

The production method and a confirmation method of the methanol solvate crystal of eucomic acid are the same as those described in the above 2.

The eucomic acid contained in the aqueous solution in which eucomic acid is dissolved may be produced by a production method of any of a chemical synthesis method, an extraction method from a natural substance, a fermentation method, an enzyme method, or the like.

When the aqueous solution in which eucomic acid is dissolved contains solids that interfere with crystallization, the solids can be removed by using centrifugation, filtration, ceramic filtering, or the like, and the aqueous solution can be used in the step of precipitating the methanol solvate crystal of eucomic acid in the aqueous solution in which eucomic acid is dissolved.

When the aqueous solution in which eucomic acid is dissolved contains water-soluble impurities or salts that interfere with crystallization, the water-soluble impurities or salts can be removed by passing through a column filled with ion exchange resin or the like, and the aqueous solution can be used in the step of precipitating the methanol solvate crystal of eucomic acid in the aqueous solution in which eucomic acid is dissolved.

When the aqueous solution in which eucomic acid is dissolved contains hydrophobic impurities or salts that interfere with crystallization, the hydrophobic impurities can be removed by passing through a column filled with synthetic adsorption resin, active carbon, or the like, and the aqueous solution can be used in the step of precipitating the methanol solvate crystal of eucomic acid in the aqueous solution in which eucomic acid is dissolved.

A concentration of the eucomic acid in the aqueous solution in which eucomic acid is dissolved can be prepared to generally 300 g/L or more, preferably 350 g/L or more, and more preferably 400 g/L or more.

The aqueous solution can be concentrated by a general concentration method such as a heating concentration method or a vacuum concentration method in order to set the concentration of the eucomic acid in the aqueous solution in which eucomic acid is dissolved to the above concentration.

When the aqueous methanol solution is dropped or added, examples of a water content of the aqueous methanol solution include generally 40 wt % or less, preferably 20 wt % or less, more preferably 10 wt % or less, and most preferably 5 wt % or less.

When methanol or the aqueous methanol solution is added or dropped into the aqueous solution in which eucomic acid is dissolved, temperature of the aqueous solution, liquid amount of methanol or the aqueous methanol solution to be dropped or added, or time required for adding or dropping methanol or the aqueous methanol solution can change with the concentration of eucomic acid in the aqueous solution and the water content of the aqueous methanol solution to be added or dropped, or the like, but may be temperature, liquid amount, and time for the methanol solvate crystal of eucomic acid to precipitate in the aqueous solution.

A person skilled in the art can appropriately set, for example, the temperature of the aqueous solution in which eucomic acid is dissolved in a range of generally 0° C. to 40° C., preferably 0° C. to 35° C., more preferably 5° C. to 30° C., the liquid amount of methanol or the aqueous methanol solution to be added or dropped in a range of generally equal to 0.1 to 100 times, preferably equal to 0.1 to 10 times, more preferably equal to 0.1 to 3 times the aqueous solution, and the time required for adding or dropping methanol or the aqueous methanol solution in a range of generally 1 minute to 24 hours, preferably 1 minute to 10 hours, and more preferably 1 to 7 hours.

A seed crystal may be added immediately before start of the step of dropping or adding methanol or the aqueous methanol solution in the aqueous solution in which eucomic acid is dissolved to precipitate the methanol solvate crystal of eucomic acid in the aqueous solution.

A seed crystal may be added before the methanol solvate crystal of eucomic acid is precipitated in the step of dropping or adding methanol or the aqueous methanol solution in the aqueous solution in which eucomic acid is dissolved to precipitate the methanol solvate crystal of eucomic acid in the aqueous solution.

As the seed crystal, for example, the methanol solvate crystal of eucomic acid obtained by the method of the above 2 can be used.

The seed crystal can be added so that a concentration thereof in the aqueous solution is generally 0.001 to 50 g/L, preferably 0.01 to 5 g/L.

Time for adding the seed crystal can be set, for example, in a range of generally 0 to 12 hours, preferably 0 to 8 hours, and more preferably 0 to 4 hours after the start of adding or dropping methanol or the aqueous methanol solution.

The precipitated crystal can be aged for generally 1 to 48 hours, preferably 1 to 24 hours, and more preferably 1 to 12 hours after precipitation of the methanol solvate crystal of eucomic acid by dropping or adding methanol or the aqueous methanol solution in the aqueous solution in which eucomic acid is dissolved.

Aging a crystal refers to growing the precipitated methanol solvate crystal of eucomic acid. Growing a crystal refers to increasing the crystal based on the precipitated crystal.

Aging of the crystal is mainly performed to grow the crystal, but a new crystal may be precipitated simultaneously with the growth of the crystal. After the crystal is aged, a step of newly precipitating the methanol solvate crystal of eucomic acid may be resumed.

In the step of collecting the methanol solvate crystal of eucomic acid, filtering, pressure filtration, suction filtration, centrifugation, or the like can be performed. Further, in order to reduce the adhesion of the mother liquor to the crystal and improve the quality of the crystal, the crystal can be washed as appropriate after collecting the crystal.

As a solution used for crystal washing, for example, a solution in which one or more selected from the group consisting of water, methanol, ethanol, acetone, n-propanol, and isopropyl alcohol are mixed at any ratio can be used.

The methanol solvate crystal of eucomic acid can be obtained by drying a collected wet crystal or a wet crystal after crystal washing.

A method for drying the wet crystal is not particularly limited as long as it can maintain the form of the methanol solvate crystal of eucomic acid, and examples thereof include drying under reduced pressure, vacuum drying, fluidized bed drying, and ventilation drying.

Drying temperature of the wet crystal may be in any range as long as the adhering moisture or solution can be removed, and examples thereof include generally 80° C. or lower, preferably 70° C. or lower, and more preferably 60° C. or lower.

Examples of drying time of the wet crystal include generally 1 to 60 hours, and preferably 1 to 48 hours.

The non-solvate crystal of eucomic acid can be obtained by further drying the methanol solvate crystal of eucomic acid obtained after drying by the method described in the above 2.

The non-solvate crystal of eucomic acid can be obtained by directly drying the collected wet crystal or the wet crystal after crystal washing by the method described in the above 2.

Purity and a detailed embodiment of the non-solvate crystal of eucomic acid which can be produced by the "production method-2 of the present invention" are the same as the purity and embodiment of the above 2.

Although Examples are shown below, the present invention is not limited to the following Examples.

EXAMPLES

Production of Non-Solvate Crystal of Eucomic Acid

In water, 340 g of eucomic acid powder having purity of 95% (area %) was dissolved to prepare a eucomic acid-containing aqueous solution a total amount of which is 750 mL. To the eucomic acid-containing aqueous solution was added 250 mL of methanol at room temperature over 2 hours, and then a crystal was precipitated. The crystal was obtained by vacuum-drying the wet crystal obtained by centrifuging an aqueous solution containing the crystal.

By analysis using HPLC, it was confirmed that the crystal was a crystal of eucomic acid. In addition, as a result of measuring residual methanol using a gas chromatograph, it was found that the crystal was a methanol solvate crystal of eucomic acid since a methanol content of the crystal was 28.1 wt %. The methanol content is a value including methanol adhering to the crystal surface. The methanol content in the crystal except for the methanol adhering to the crystal surface was 9.0 wt %. It was considered from this that the crystal was a mono-methanol solvate crystal of eucomic acid.

Subsequently, the obtained methanol solvate crystal of eucomic acid was heated and dried at 100° C. for 9 hours at normal pressure. By analysis using HPLC, it was confirmed that the crystal after heating and drying was a crystal of eucomic acid. As a result of measuring the water content by a Karl Fischer method, it was confirmed that the crystal did not contain hydrated water. As a result of measuring residual methanol using a gas chromatograph, a methanol content of the crystal was 0.14 wt %. It was found from the above that the crystal was a non-solvate crystal of eucomic acid.

Further, by measuring purity by HPLC, it was confirmed that the obtained non-solvate crystal of eucomic acid had eucomic acid purity of 98% (area %) or more.

Table 1 shows diffraction angles of peaks in which a relative intensity ratio ($I/I_0$) was 10 or more from results of powder X-ray diffraction of the obtained non-solvate crystal of eucomic acid. In the table, "$2\theta$" represents a diffraction angle $2\theta(°)$, and "relative intensity" represents a relative intensity ratio. Results of powder X-ray diffraction of the obtained non-solvate crystal of eucomic acid using CuKα as the X-ray source are shown in FIG. 1, and results of infrared (IR) spectroscopic analysis are shown in FIG. 2.

TABLE 1

| $2\theta$ | Relative intensity |
| --- | --- |
| 10.9 | 18 |
| 13.1 | 100 |
| 16.1 | 10 |
| 18.2 | 14 |
| 18.7 | 100 |
| 21.8 | 97 |
| 22.6 | 22 |
| 23.5 | 10 |
| 26.3 | 12 |
| 26.7 | 15 |
| 27.6 | 15 |
| 31.1 | 11 |
| 31.4 | 10 |
| 33.3 | 13 |
| 33.8 | 21 |
| 34.8 | 12 |
| 36.9 | 11 |
| 37.3 | 13 |
| 38.6 | 11 |

Subsequently, powder properties of the obtained methanol solvate crystal and non-solvate crystal of eucomic acid were measured. A summary of measurement results of the methanol content and the powder properties of the two crystals are shown in Table 2.

TABLE 2

|  | Methanol content (wt %) | Angle of repose (degree) | Uniformity coefficient (–) |
| --- | --- | --- | --- |
| Methanol solvate crystal | 28.1 | 45.7 | 4.25 |
| Non-solvate crystal | 0.14 | 39.0 | 3.36 |

As shown in Table 2, since the non-solvate crystal had a smaller angle of repose and a uniformity coefficient closer to 1 than the methanol solvate crystal, it was found that the non-solvate crystal had excellent fluidity as compared with the methanol solvate crystal.

Although the present invention has been described in detail with reference to specific embodiments, it will be apparent to those skilled in the art that various modifications and variations are possible without departing from the spirit and scope of the present invention. The present application is based on Japanese Patent Application No. 2018-133057 filed on Jul. 13, 2018, the contents of which are incorporated herein by reference. In addition, all references cited herein are incorporated in their entirety.

INDUSTRIAL APPLICABILITY

The present invention provides a non-solvate crystal of eucomic acid having a low methanol content and excellent fluidity, and a method for producing the same.

The invention claimed is:

1. A non-solvate crystal of eucomic acid, which has peaks at diffraction angle $2\theta$ (°) of 13.1°±0.2°, 18.7°±0.2°, and 21.8°±0.2° in powder X-ray diffraction.

2. The crystal according to claim 1, which further has peaks at diffraction angle $2\theta$ (°) of 22.6°±0.2°, 33.8°±0.2°, and 10.9°±0.2° in powder X-ray diffraction.

3. The crystal according to claim 2, which further has peaks at diffraction angle $2\theta$ (°) of 26.7°±0.2°, 27.6°±0.2°, and 18.2°±0.2° in powder X-ray diffraction.

4. The crystal according to claim 3, which further has peaks at diffraction angle $2\theta$ (°) of 33.3°±0.2°, 37.3°±0.2°, 26.3°±0.2°, and 34.8°±0.2° in powder X-ray diffraction.

5. The crystal according to claim 4, which further has peaks at diffraction angle $2\theta$ (°) of 31.1°±0.2°, 36.9°±0.2°, and 38.6°±0.2° in powder X-ray diffraction.

6. The crystal according to claim 5, which further has peaks at diffraction angle $2\theta$ (°) of 16.1°±0.2°, 23.5°±0.2°, and 31.4°±0.2° in powder X-ray diffraction.

7. A method for producing the non-solvate crystal of eucomic acid of claim 1, comprising a step of dropping or adding methanol or an aqueous methanol solution to an aqueous solution in which eucomic acid is dissolved to precipitate a methanol solvate crystal of eucomic acid in the aqueous solution; a step of collecting the methanol solvate crystal of eucomic acid from the aqueous solution; and a step of drying the collected methanol solvate crystal of eucomic acid.

* * * * *